United States Patent [19]

Foux

[11] 4,160,454
[45] Jul. 10, 1979

[54] IMPLANTABLE CATHETER SYSTEM

[75] Inventor: Amnon Foux, Haifa, Israel

[73] Assignee: University of Utah, Salt Lake City, Utah

[21] Appl. No.: 768,520

[22] Filed: Feb. 14, 1977

Related U.S. Application Data

[63] Continuation of Ser. No. 594,374, Jul. 9, 1975, abandoned.

[51] Int. Cl.² .................... A61M 25/00; A61M 05/00
[52] U.S. Cl. ................................... 128/348; 128/215; 128/260
[58] Field of Search .................. 128/348–350 V, 128/215, 216, 231–232, 1 R, 260, 275; 3/1

[56] References Cited

U.S. PATENT DOCUMENTS

| | | | |
|---|---|---|---|
| 3,136,316 | 6/1964 | Beall | 128/350 R |
| 3,310,051 | 3/1967 | Schulte | 128/216 |
| 3,640,269 | 2/1972 | Delgado | 128/348 X |
| 3,707,967 | 1/1973 | Kitrilakis et al. | 128/348 X |
| 3,853,126 | 12/1974 | Schulte | 128/348 X |
| 3,885,561 | 5/1975 | Cami | 128/349 R X |
| 3,971,376 | 7/1976 | Wichterle | 128/260 |

*Primary Examiner*—Dalton L. Truluck
*Attorney, Agent, or Firm*—Criddle, Thorpe & Western

[57] ABSTRACT

An implantable catheter system includes an elongated hollow casing which is reinforced to maintain a predetermined attitude and made of a material penetrable by a needle, and a tube extending laterally of the casing so that when the casing is implanted subcutaneously in a person, the tube may extend into the person's peritoneal cavity. The tube is coupled into the casing to enable communication therebetween. The free end of the tube includes a plurality of openings to enable the flow of fluid therethrough into or out of the tube. When the catheter system is implanted in the body of a person, fluids may be introduced into and withdrawn from the peritoneal cavity by inserting a hypodermic needle through the epidermis of a person into the casing which is implanted subcutaneously in the person. Fluid is then injected into or withdrawn from the casing to thereby respectively force fluid through the tube into the peritoneal cavity or withdraw fluid from the cavity via the tube.

10 Claims, 4 Drawing Figures

IMPLANTABLE CATHETER SYSTEM

This is a continuation of application Ser. No. 594,374, filed July 9, 1975 now abandoned.

BACKGROUND OF THE INVENTION

This invention relates to a system and method for introducing fluids into and withdrawing fluids from body cavities such as the peritoneal cavity.

Prior art methods of introducing liquids into human body cavities and of withdrawing liquids therefrom include simply the use of a disposable catheter inserted through a person's skin, subcutaneous fat, fascia, muscles, etc. or through an implantable collar into the body cavity of interest. Another method involves the use of a catheter implanted in the person's body so that one end extends into the cavity and the other end protrudes through the epidermis of the person. In the former method where the catheter is inserted through the person's skin, etc., each time liquid is to be introduced or withdrawn, the disposable catheter must be inserted to extend into the body cavity in question, such as the peritoneal cavity, and then remain in place while the liquid is introduced or withdrawn. This arrangement is painful to the person and results in permanent damage to the tissue and membranes through which the catheter must repeatedly penetrate. The latter method, one example of which uses the Tenckhoff peritoneal dialysis catheter system, overcomes some of the disadvantages present with the use of the disposable catheter but nevertheless presents other problems because one end of the implanted catheter tube is permanently exposed through the person's skin. Such problems include infection in the tissue surrounding the protruding end of the catheter, infection in the peritoneal cavity caused by bacteria penetrating through the protruding end, discomfort from the need to protect and seal the protruding end of the catheter, and embarrassment from public exposure of the implanted catheter tube.

SUMMARY OF THE INVENTION

It is an object of the present invention to provide an implantable catheter system and method for efficiently introducing fluids into and withdrawing fluids from body cavities.

It is also an object of the present invention to provide such a system and method in which the possibility of infection is minimized.

It is another object of the present invention to provide such a system and method which causes little physical discomfort or embarrassment to a patient.

The above and other objects of the present invention are realized in a specific illustrative embodiment of an implantable catheter system which includes a hollow member adapted for subcutaneous implantation in a person. The system also includes a tubular member, one end of which is coupled into the hollow member to enable communication therebetween and the other end of which has at least one opening to enable the flow of fluid therethrough into or out of the tubular member. The tubular member is of sufficient length so that when the hollow member is implanted subcutaneously, the tubular member extends into the body cavity of interest. The hollow member is constructed of a material which is penetrable by a needle and which is reinforced to prevent collapse thereof when fluid is withdrawn from the member.

The implantable catheter system is used for introducing fluid into a body cavity by implanting the hollow member of the system subcutaneously in a person so that the tubular member extends into the body cavity in question. The fluid is then introduced into the cavity or withdrawn from the cavity by inserting a hypodermic needle through the epidermis of the person into the hollow member and then either applying fluid to the hollow member or withdrawing fluid therefrom. Fluid therefore either flows from the hollow member through the tubular member into the body cavity or is drawn from the body cavity through the tubular member into the hollow member as the case may be. With this arrangement, only the epidermis and subcutaneous fat of a person is punctured by the needle and no part of the catheter system is exposed through the person's skin.

BRIEF DESCRIPTION OF THE DRAWINGS

The above and other objects, features and advantages of the present invention will become apparent from a consideration of the following detailed description presented in connection with the accompanying drawings in which.

DETAILED DESCRIPTION

Figure 1:
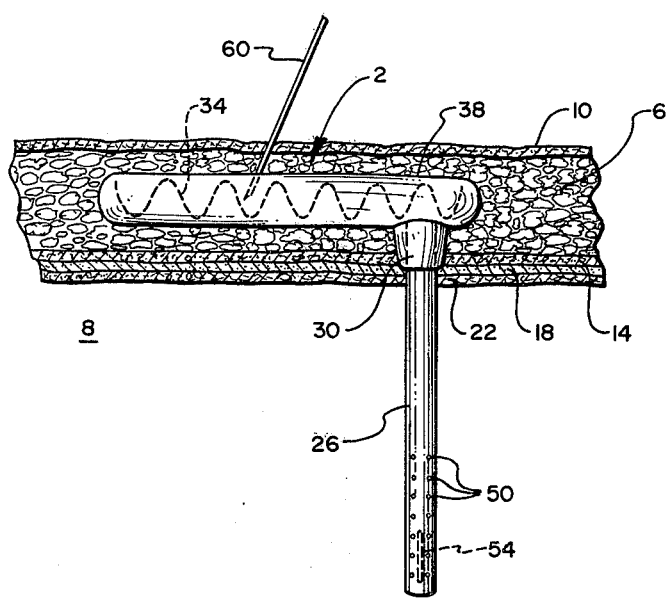
FIG. 1 is a side view of a single-catheter embodiment of the present invention shown implanted in the subcutaneous fat of a person.

The single-catheter embodiment of the implantable catheter system of the present invention, shown in FIG. 1, includes an elongated hollow member or casing 2 shown implanted in the subcutaneous fat layer 6 of a person. Such a layer is located between a person's epidermis 10 and fascia 14. Below the fascia is shown muscle tissue 18 and a peritoneal membrane 22 which encloses a person's peritoneal cavity 8.

Extending generally laterally from one end of the casing 2 is a tube 26. One end of the tube is fitted through an opening into the casing 2 and held in place by a collar 30 and a suitable adhesive. The interior of the tube 26 communicates with the interior of the casing 2. Of course, it will be understood the tube 26 could be integral with the casing 2.

The tube 26 is of sufficient length so that when the casing 2 is implanted subcutaneously (beneath the skin) which, in FIG. 1, is in the subcutaneous fat, the tube 26 may extend through the fascia 14, muscle tissue 18 and peritoneal membrane 22 into the desired location in the peritoneal cavity (or into whatever body cavity is of interest).

The casing 2 is made of a material which is penetrable by a hypodermic needle 60, such as silastic rubber. To prevent collapse of the casing 2, either when a needle is inserted or when liquid is withdrawn from the casing, and maintain the casing in a predetermined attitude, the casing is reinforced by a coil of wire 34 (shown by dotted line in FIG. 1). Preferably, a stainless steel wire spiral is utilized because of the strength and general deterioration immunity of stainless steel. Of course, a variety of arrangements could be used to reinforce the casing 2.

Figure 2:
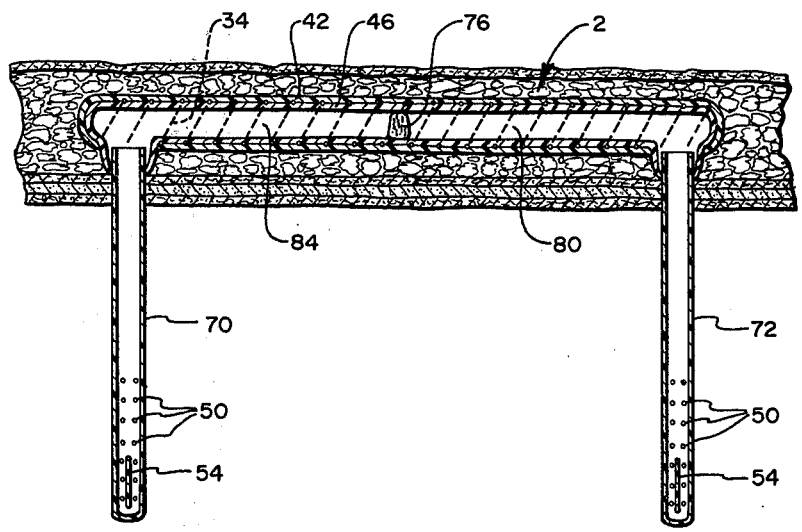
FIG. 2 is a side cross-sectional view of a double-catheter embodiment of the present invention.

One specific illustrative embodiment of a casing structure is shown in FIG. 2. In this structure, the stainless steel reinforcing wire spiral 34 is embedded in the wall of the casing 2 to maintain the casing in the predetermined attitude. The rest of the structure of the catheter system of FIG. 2 will be described later.

The exterior of the casing 2 (FIG. 1) is formed to present a generally rough or porous surface 38 to enable the growth of human tissue thereon. For example, an exterior layer of the casing 2 may be a polyester resin velour or a porous polytetrafluoroethylene. Advantageously the exterior surface 38 is treated to enhance and accelerate the growth of human tissue thereon. One method of treating the surface 38 is by radio frequency glow discharge as described in a master's thesis entitled "Measurements of Cellular Adhesion of Glass and Polymer Substrates", of Lee Smith, University of Utah, Department of Mechanical Engineering, June, 1973. The purpose of the tissue growth enhancing material will be discussed momentarily.

The tube 26 includes a plurality of openings 50 located near the free end of the tube to allow the flow of liquid through the openings into or out of the tube 26. Advantageously, the tube 26 is made of flexible silicone rubber. Disposed in the end of the tube 26 is a piece of stainless steel 54 or other X-ray detectable material. This facilitates locating and tracing the movement of the tip of the tube 26 during an implantation operation to insure its proper positioning.

Figure 3:
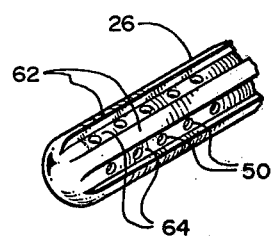
FIG. 3 is a fragmented, perspective view of one embodiment of the end of the tube 26 of FIG. 1.

FIG. 3 shows one embodiment of the end of the tube 26 adapted to facilitate the flow of liquid through openings 50 even if the tube is positioned against body tissue. The exterior of the tube 26 is formed with alternating ridges 62 and grooves 64, with the openings 50 disposed in the grooves. With this structure, liquid may generally flow through the openings and along the grooves 64 (and vice-versa) even though the tube 26 is positioned against body tissue. The ridges 62 function to hold tissue (for example of an internal body organ) away from the openings 50 so that the openings will not be "stopped up". Although ridges 62 and grooves 64 are shown extending longitudinally along the tube 26 in FIG. 3, it is apparent that the ridges and grooves could extend circumferentially about the tube, diagonally about the tube, etc. Further, the ridges 62 might be replaced simply by any type of protuberance which projects outwardly of the tube above the openings.

In use, for example such as in intermittent flow peritoneal dialysis, the catheter system shown in FIG. 1 is implanted subcutaneously in the body of a person so that the tubular member 26 extends into and is properly positioned in the peritoneal cavity 8 of the person. After the catheter system is implanted, liquids, such as dialysis solution, may be introduced into or withdrawn from the peritoneal cavity. Introduction of such liquid is accomplished by inserting a hypodermic needle 60 through the epidermis 10 into the casing 2 and then, once inserted, the liquid is introduced through the hypodermic needle 60 into the hollow of the casing. The liquid thereby flows through the tube 26 out the openings 50 into the peritoneal cavity 8. After introduction of the liquid, the needle 60 may be withdrawn leaving only a readily healable wound in the epidermis 10, or left in place for subsequent use in introducing more liquid into or withdrawing liquid from the peritoneal cavity. If the needle 60 is withdrawn, the hole left in the casing wall 2 is rapidly sealed by tissue growth. The tissue grows on the surface 38 and over the hole in the casing 2 to prevent outflow of any liquid through the hole.

Shown in FIG. 2 is a side cross-sectional view of a double-catheter system which includes a casing 2 and a pair of tubes 70 and 72 extending generally laterally from either end thereof in a substantially parallel relationship. A plug 76 is disposed in the casing to divide the hollow defined by the casing into separate portions 80 and 84, each of which is in communication with a different one of said tubes 70 and 72. The plug 76 is liquid impervious to prevent communication between the two portions 80 and 84. The tube 70 and 72 each have a plurality of openings 50 located near the free ends thereof to allow liquid to flow into and out of the tubes. Also included in the end of each tube 70 and 72 is a piece of X-ray detectable material 54 to assist in guiding the tubes during the implantation operation.

With the double-catheter system of FIG. 2, liquids may be introduced into and withdrawn from the peritoneal cavity at the same time to provide, for example, a type of continuous flow peritoneal dialysis. That is, a hypodermic needle may be inserted through the wall of the casing 2 into the portion 80 of the casing hollow to introduce fluid thereinto; a hypodermic needle may also be inserted through the wall of casing 2 into the portion 84 to withdraw fluid therefrom. The liquid thus flows from the portion 80 through the tube 72 and out the openings 50 into the peritoneal cavity; and liquid is withdrawn from the peritoneal cavity via the tube 70 and portion 84 into the hypodermic needle.

Figure 4:
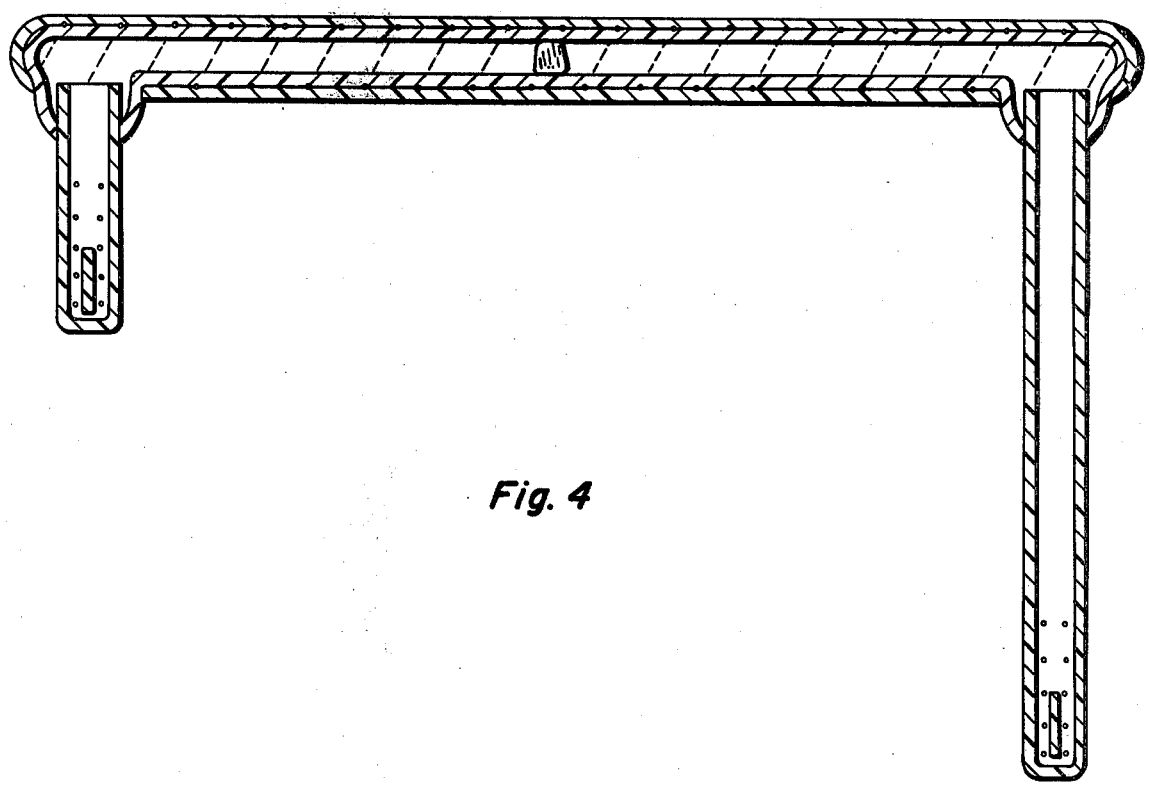
FIG. 4 is a side cross-sectional view of a double-catheter embodiment of the present invention in which one of the tubes is shorter than the other.

Note, referring to FIG. 2, the length of one of the tubes 70 or 72 may be greater than that of the other tube to better space the locations at which fluid is introduced into a body cavity and withdrawn from the body cavity. FIG. 4 shows such an arrangement.

The implantable catheter systems described provide an efficient and simple method of introducing fluids into body cavities and withdrawing fluids therefrom, such as in peritoneal dialysis. This method yields cosmetic and health advantages not obtainable with the prior art arrangements.

It is to be understood that the above-described arrangement is only illustrative of the application of the principles of the present invention. Numerous other modifications and alternative arrangements may be devised by those skilled in the art without departing from the spirit and scope of the present invention and the appended claims are intended to cover such modifications and arrangements.

What is claimed is:

1. An implantable catheter comprising
   an elongate hollow member adapted for subcutaneous placement in a person, said member being constructed of a material which is penetrable by a needle, the hollow of the member being divided into two portions neither of which is in communication with the other, said hollow member including wire coil reinforcing structure extending about the hollow of said hollow member to prevent collapse of the member when fluid is withdrawn therefrom,
   a first tubular member extending from near one end of said hollow member to enable communication between the tubular member and one of said hollow portions, and
   a second tubular member extending from near the other end of said hollow member to enable communication between the second tubular member and the other of said hollow portions, said second tubular member being spaced apart from and having a different length than said first tubular member, each of said tubular members having at least one opening therein to enable the flow of fluid between the interior and the exterior of said tubular members, the tubular members further including protuberances on the exterior surface thereof to project above the openings, and the exterior surface of said hollow member being adapted to accommodate human tissue growth thereon.

2. A catheter as in claim 1 wherein said wire coil is comprised of stainless steel.

3. A catheter as in claim 1 wherein said hollow member and said tubular members are constructed of a flexible material.

4. A catheter as in claim 1 wherein said hollow member includes an exterior layer of polyester resin velour.

5. A catheter as in claim 1 wherein said hollow member includes an exterior layer of porous polytetrafluoroethylene.

6. A catheter as in claim 1 wherein the exterior surface of said hollow member is treated to enhance and accelerate the growth of human tissue thereon.

7. A catheter as in claim 1 wherein said protuberances comprise generally parallel ridges and wherein said opening is disposed between the ridges.

8. A catheter as in claim 1 further including an X-ray detectable material disposed in the end of said tubular members.

9. A catheter as in claim 8 wherein said X-ray detectable material is comprised of stainless steel.

10. A catheter as in claim 1 wherein said catheter includes a partition in said hollow member to divide the hollow into said two portions and to prevent communication therebetween, each portion being located in a different end of said hollow member.

* * * * *